USO11849959B2

(12) United States Patent
Cha et al.

(10) Patent No.: US 11,849,959 B2
(45) Date of Patent: Dec. 26, 2023

(54) MEDICAL SCREW OPERATION DEVICE, ROBOT AND METHOD

(71) Applicants: CUREXO, INC., Seoul (KR); INDUSTRY-ACADEMIC COOPERATION FOUNDATION, YONSEI UNIVERSITY, Seoul (KR)

(72) Inventors: Yong Yeob Cha, Seoul (KR); Hong Ho Kim, Seongnam-si (KR); Seong Yi, Seoul (KR)

(73) Assignees: CUREXO, INC., Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 688 days.

(21) Appl. No.: 16/965,207

(22) PCT Filed: Feb. 12, 2019

(86) PCT No.: PCT/KR2019/001664
§ 371 (c)(1),
(2) Date: Jul. 27, 2020

(87) PCT Pub. No.: WO2019/160291
PCT Pub. Date: Aug. 22, 2019

(65) Prior Publication Data
US 2021/0059692 A1 Mar. 4, 2021

(30) Foreign Application Priority Data
Feb. 13, 2018 (KR) ........................ 10-2018-0017938

(51) Int. Cl.
*A61B 17/17* (2006.01)
*A61B 17/70* (2006.01)
(Continued)

(52) U.S. Cl.
CPC ...... *A61B 17/1757* (2013.01); *A61B 17/1735* (2013.01); *A61B 17/7082* (2013.01);
(Continued)

(58) Field of Classification Search
CPC ............ A61B 17/1757; A61B 17/1735; A61B 17/7082; A61B 34/30; A61B 2017/00367; A61B 2017/00477
(Continued)

(56) References Cited

U.S. PATENT DOCUMENTS 4,979,949 A * 12/1990 Matsen, III ............ A61G 13/12
606/88
8,814,880 B2 8/2014 McAllister et al.
(Continued)

FOREIGN PATENT DOCUMENTS

GB 2551581 A 12/2017
JP 2009-535181 A 10/2009
(Continued)

*Primary Examiner* — Eduardo C Robert
*Assistant Examiner* — David C Comstock
(74) *Attorney, Agent, or Firm* — Bridgeway IP Law Group, PLLC; Jihun Kim

(57) ABSTRACT

A medical screw surgical device includes: a surgical device main body shaped like a bar and internally formed with an insertion passage; an extension member provided in a lower portion of the surgical device main body and internally formed with a guide hole; a guide member movably provided in the guide hole of the extension member; and a firing member provided in the insertion passage of the surgical device main body and controlling the guide member to move up and down. A surgical robot having a robot arm with the medical screw surgical device includes: a support arm provided in the robot arm; a surgical device holding member provided in the support arm; and the medical screw surgical device provided in the surgical device holding member.

18 Claims, 17 Drawing Sheets

(51) Int. Cl.
*A61B 34/30* (2016.01)
*A61B 17/00* (2006.01)
(52) U.S. Cl.
CPC .... *A61B 34/30* (2016.02); *A61B 2017/00367* (2013.01); *A61B 2017/00477* (2013.01)
(58) Field of Classification Search
USPC ..... 606/279, 264, 305, 308, 80, 96, 99, 104, 606/86 A
See application file for complete search history.

(56) References Cited

U.S. PATENT DOCUMENTS

| | | |
|---|---|---|
| 9,433,445 B2 | 9/2016 | Ramsay et al. |
| 9,539,012 B2* | 1/2017 | Landry .............. A61B 17/1671 |
| 2001/0027320 A1* | 10/2001 | Sasso ................ A61B 17/1735 606/96 |
| 2006/0079903 A1 | 4/2006 | Wong |
| 2008/0161814 A1 | 7/2008 | Steven et al. |
| 2008/0293010 A1 | 11/2008 | Song |
| 2009/0275994 A1 | 11/2009 | Phan et al. |
| 2010/0211115 A1 | 8/2010 | Gannoe et al. |
| 2016/0287306 A1 | 10/2016 | Meier et al. |
| 2017/0312039 A1* | 11/2017 | Crawford ........... A61B 17/1604 |
| 2018/0014890 A1 | 1/2018 | Stanton et al. |
| 2018/0200016 A1* | 7/2018 | Chappuis ............... A61B 34/30 |

FOREIGN PATENT DOCUMENTS

| | | |
|---|---|---|
| KR | 10-1001539 B1 | 12/2010 |
| KR | 10-1083889 B1 | 11/2011 |
| KR | 10-1631908 B1 | 6/2016 |
| WO | 2007/130891 A1 | 11/2007 |

* cited by examiner

MEDICAL SCREW OPERATION DEVICE, ROBOT AND METHOD

TECHNICAL FIELD

The disclosure relates to a medical screw surgical device, a surgical robot with the same, and a surgical method of using the surgical robot with the medical screw surgical device, and more particularly to a medical screw surgical device, a surgical robot with the same, and a surgical method of using the surgical robot with the medical screw surgical device, by which time taken in surgery is shortened by simplifying surgical procedures, in particular, pedicle screw insertion surgery is quickly and easily performed, and accuracy of surgery is improved.

BACKGROUND ART

In general, a spine supporting a human body is made up of 24 vertebrae, a disc lies between adjacent vertebrae, and nerves cross the vertebrae.

Further, when the spine is artificially damaged or is damaged or twisted by degenerative changes or wrong postures, the nerves crossing the spine are pressed to thereby cause acute pain. A slight pain is treated based on physical therapy, but a severe pain needs to undergo a surgical operation that corrects the posture of the spine by inserting a fixation device for immobilizing pedicles or releases the pressure on the nerves.

The pedicle screw insertion surgery is performed by inserting pedicle screws into a plurality of pedicles, and connecting the adjacent pedicle screws with a rod to achieve spinal fusion.

The pedicle screw insertion surgery realigns the spine by widening a space between the pedicle compressing the nerve and the adjacent pedicle with a rod and thus prevents the pedicle from compressing the nerve.

Further, a pedicle screw used in the pedicle screw insertion surgery includes a screw head shaped like a cup and formed with a seating groove opened upward to seat the road thereon, and a screw body rotatably coupled to the bottom of the screw head and formed with a thread to be screw-coupled to the pedicle.

Meanwhile, as described above, the pedicle screw insertion surgery is carried out by inserting the pedicle screws into a plurality of pedicles with a fastening tool called a driver and then connecting the screw heads of the pedicle screws with the rod, but has limitations that procedures up to the insertion of the pedicle screws into the pedicles are very complicated and many kinds of surgical instruments are required.

For example, conventional procedures and surgical instruments for the pedicle screw insertion surgery are as follows. A process of inserting the pedicle screw refers to inserting a pedicle screw S into a pedicle P as shown in FIG. 1C using a plurality of surgical instruments as shown in FIGS. 1A and 1B, and is completed by taking many procedures and steps in sequence as shown in FIGS. 1D and 1E.

In the procedures of inserting the pedicle screw in the conventional pedicle screw insertion surgery, there are performed a first step S1 of inserting a guide pin i1 with a grip (typically called a 'VP needle') into the pedicle P by a strike with a hammer T3 as shown in FIGS. 1D and 1E while taking an image through radiography equipment, a second step S2 of inserting a reference wire i2 (K-wire) for correctly guiding the insertion of the pedicle screw S through a hollow formed in a needle portion of the guide pin i1 inserted in the first step S1, a third step S3 of removing the guide pin i1 from the reference wire i2, a fourth step S4 of inserting a first sleeve i3 in the outer circumferential surface of the reference wire i2, and a fifth step S5 of inserting a second sleeve i4 in the outer circumferential surface of the first sleeve i3.

Then, there are performed a sixth step S6 of removing the first sleeve i3 positioned inside the second sleeve i4, a seventh step S7 of inserting a reamer T1 (i.e. an operation tool) into the second sleeve i4 and carrying out reaming and tapping, an eighth step of separating and removing the reamer T1 that completes the seventh step, a ninth step S9 of inserting a third sleeve i5 in the outside of the second sleeve i4, a tenth step S10 of removing the second sleeve i4 when the installation of the third sleeve i5 is completed, an eleventh step S11 and S12 of inserting the driver T2 mounted with the pedicle screw C into the inside of the third sleeve i5 and loading the pedicle screw in a screw coupling hole P2 formed in the pedicle P (S11) and performing a coupling operation (S12), and a twelfth step S13 of removing the driver T2 and the third sleeve i5 and finishing.

In the foregoing conventional pedicle screw insertion surgery, the process of inserting the pedicle screw has a problem that it takes long time to perform the surgery and repetitive jobs increase fatigue of a medical team because of very complicated and excessively many surgical procedures of about twelve steps, and has shortcomings that a burden of medical expenses on a patient is increased because not only many kinds of surgical instruments such as the guide pin i1, the reference wire i2, the first sleeve i3, the second sleeve i4, the third sleeve i5, the reamer T1, the screw driver T2, the hammer T3, etc. as shown in FIGS. 1A and 1B are required in surgery, but also management and maintenance of the surgical devices cause surgical costs to rise.

In particular, the accuracy, quality, and patient recovery of conventional pedicle screw insertion surgery vary depending on the qualifications of the medical team. This is primarily attributed to the manual performance of tasks such as insertion route setting, correction and maintenance of position and posture, and the utilization of various surgical instruments like the reference wire i2, sleeves i3, i4, i5, and others. However, the limitations of the conventional pedicle screw insertion surgery are evident. One issue arises during the reaming or tapping procedure using the first to third sleeves, where the K-wire and other surgical instruments may unintentionally be inserted too deeply. This problem becomes even more concerning as it significantly increases the likelihood of a fatal medical accident occurring. In addition, the conventional pedicle screw insertion surgery has a problem that a patient or a medical team are exposed to radiation because repetitive radiography is involved in the process of inserting the K-wire i2 or the like.

DISCLOSURE

Technical Problem

The disclosure has been proposed as conceived from the foregoing grounds, and an aspect of the disclosure is to provide a medical screw surgical device, a surgical robot with the same, and a surgical method of using the surgical robot with the medical screw surgical device, by which time taken in surgery is shortened with a simple surgical process, surgery is easily performed with simple surgical instruments, and medical expenses are reduced.

Another aspect of the disclosure is to provide a medical screw surgical device, a surgical robot with the same, and a surgical method of using the surgical robot with the medical screw surgical device, by which the robot is used to quickly and easily perform a pedicle screw insertion surgery and improve accuracy of surgery.

Technical Solution

According to an embodiment of the disclosure, the medical screw surgical device includes: a surgical device main body formed with an insertion passage inside a bar-shaped body; an extension member provided in a lower portion of the surgical device main body and internally formed with a guide hole; a guide member movably provided in the guide hole of the extension member; and a firing member provided in the insertion passage of the surgical device main body and controlling the guide member to move up and down.

In addition, the medical screw surgical device may further include a tool connecting member provided in an upper portion of the surgical device main body and connecting with an operation tool for applying a tightening force and a releasing force to the surgical device main body.

The tool connecting member includes a connection body and a fixing bolt, the connection body including a main body connector which is inserted in a top portion of the surgical device main body and formed with a fixing-bolt insertion hole, and a tool connector to which the operation tool is connected, and the fixing bolt being inserted in the fixing-bolt insertion hole of the connection body, and the surgical device main body may include a fixing bolt fastening hole in an upper portion thereof to which the fixing bolt is fastened.

Preferably, the guide member may include a thread formed on an outer circumferential surface of a guide body shaped like a pin, and the extension member may include a thread formed on an outer circumferential surface of an extension member body shaped like a pin in an opposite direction to the guide member.

The guide member may include a stopper protrusion formed in a top portion of the guide body, and the extension member may include a protrusion-movement hole formed to have a cross-section corresponding to a cross-section of the stopper protrusion and communicating with the guide hole.

The extension member may include a cut-open portion having a height difference on the outer circumferential surface of the extension member body, and the insertion passage of the surgical device main body may be formed with a cut-open portion insertion hole in which the cut-open portion is inserted and seated.

The firing member may include a firing member body shaped like a bar, a support bar protruding from a bottom portion of the firing member body and being in contact with the top portion of the guide member, and a moving piece formed in a top portion of the firing member body, and the surgical device main body may include a movement guiding groove, which allows the moving piece to move up and down, and holding grooves, which communicate with the movement guiding groove and hold the moving piece in position, are formed to communicate with the insertion passage thereof.

According to an embodiment of the disclosure, a surgical robot with a robot arm includes: a support arm provided in the robot arm; a surgical device holding member provided in the support arm; and the foregoing medical screw surgical device provided in the surgical device holding member.

Preferably, the support arm may be structured to include a coupling hole at an end portion of the support arm body including a curved portion, and the surgical device holding member may include a sleeve holder inserted in and locked to the coupling hole and formed with a sleeve insertion hole, and a sleeve inserted in the sleeve holder and including a surgical device insertion hole.

Meanwhile, according to an embodiment of the disclosure, a surgical method of using the surgical robot with the medical screw surgical device includes: a surgical-device mounting step of mounting the surgical device holding member to the support arm and mounting the medical screw surgical device with an operation tool; a guide-member inserting step of controlling the firing member in a forward direction to move down and hold the guide member and controlling the operation tool to insert the guide member into a surgical site; a guide-member releasing step of controlling the firing member in a reverse direction to release a binding force applied to the guide member so that the guide member can move up; an extension-member inserting step of applying the tightening force to the operation tool after carrying out the guide-member releasing step so that the extension member can ream and tap a surgical site and form the screw insertion hole; and a medical-screw inserting step of removing the operation tool including the medical screw surgical device, installing and fastening the screw coupling tool with the medical screw to the surgical device holding member, and removing the screw coupling tool.

Preferably, the guide-member inserting step may be carried out by rotating the guide member in a certain direction based on the screw portion formed on the outer circumferential surface of the guide body shaped like a pin.

The extension-member inserting step may be carried out by rotating the extension member in an opposite direction to the rotating direction for inserting the guide member, based on the screw portion formed on the outer circumferential surface of the extension member body shaped like a pin in the opposite direction to the guide member.

Advantageous Effects

By a medical screw surgical device according to the disclosure, a surgical robot with the same, and a surgical method of using the surgical robot with the medical screw surgical device, time taken in surgery is shortened with simple surgical procedures, and improvement in surgical efficiency and reduction of management and maintenance costs are achieved with concise and simple surgical instruments without excessively many kinds of surgical instruments such as the guide pin, the reference wire, the first sleeve, the second sleeve, the third sleeve, the reamer, the hammer, etc. which have been conventionally required in the surgery, thereby having effects on enhancing medical quality and decreasing a burden of medical expenses on a patient.

Further, by a medical screw surgical device according to the disclosure, a surgical robot with the same, and a surgical method of using the surgical robot with the medical screw surgical device, a specially devised medical screw surgical device is mounted to the robot arm of the surgical robot to insert the medical screw, thereby omitting, reducing or simplifying the process based on manual operations using a hammer or the like. Further, it is possible to solve the conventional problem that the surgical device is unintentionally deeply inserted. The medical screw is inserted through guide operations of the surgical robot, thereby preventing a defective surgery and securing accuracy. Radiography is minimized, thereby having advantages of reducing exposure to radiation.

BEST MODE

Figure 1A:
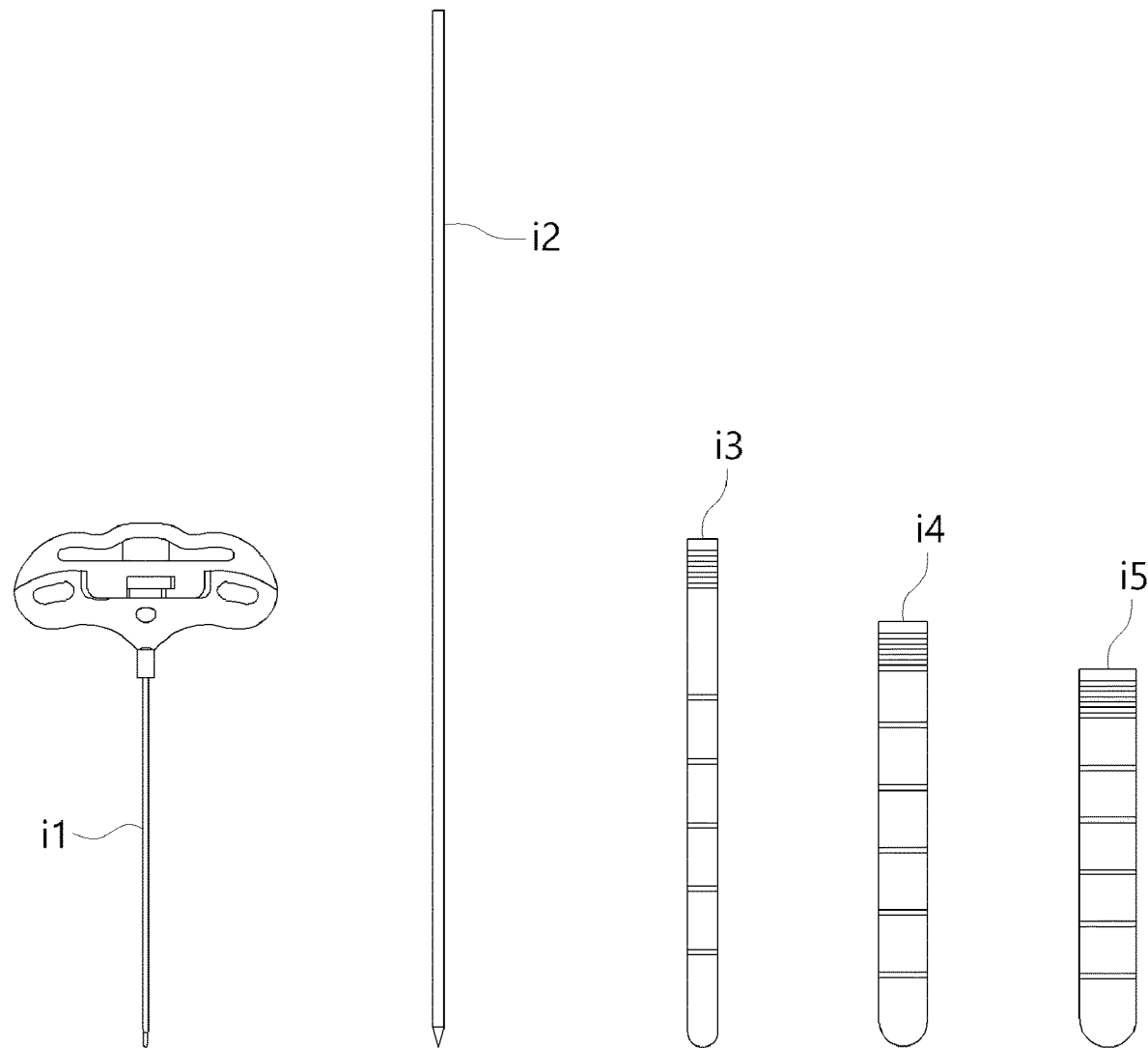
FIGS. 1A and 1B are views for explaining surgical devices used in a conventional pedicle screw insertion surgery.
Figure 1B:
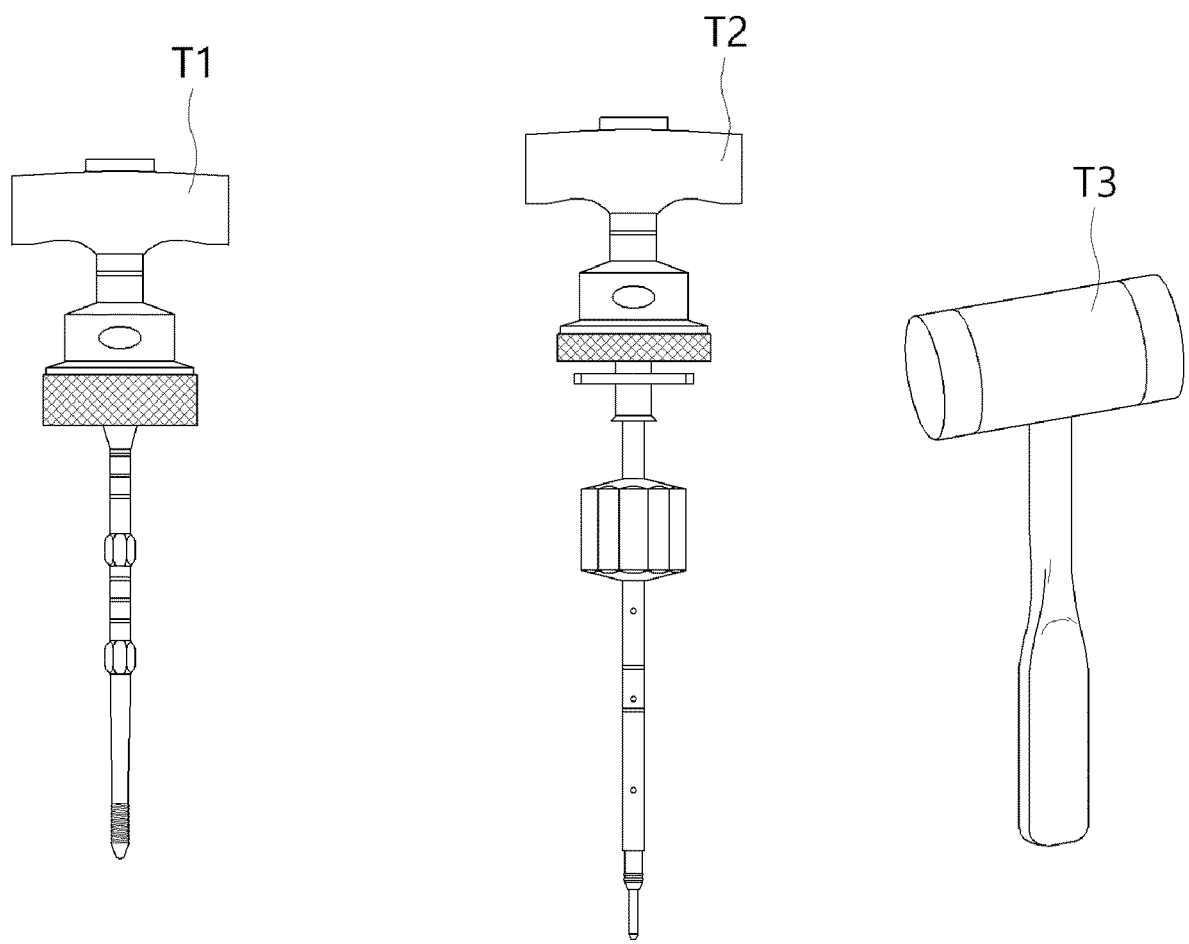

Below, exemplary embodiments of the disclosure will be described in detail based on the accompanying drawings FIGS. 2 to 8C, in which like numerals refer to like elements throughout FIGS. 2 to 8C. Meanwhile, illustrations and detailed descriptions about the elements that can be easily understood by those skilled in this field from the general art and the operations and effects thereof are simplified and omitted in the drawings, and illustration is made focusing on parts related to the disclosure.

Figure 2:
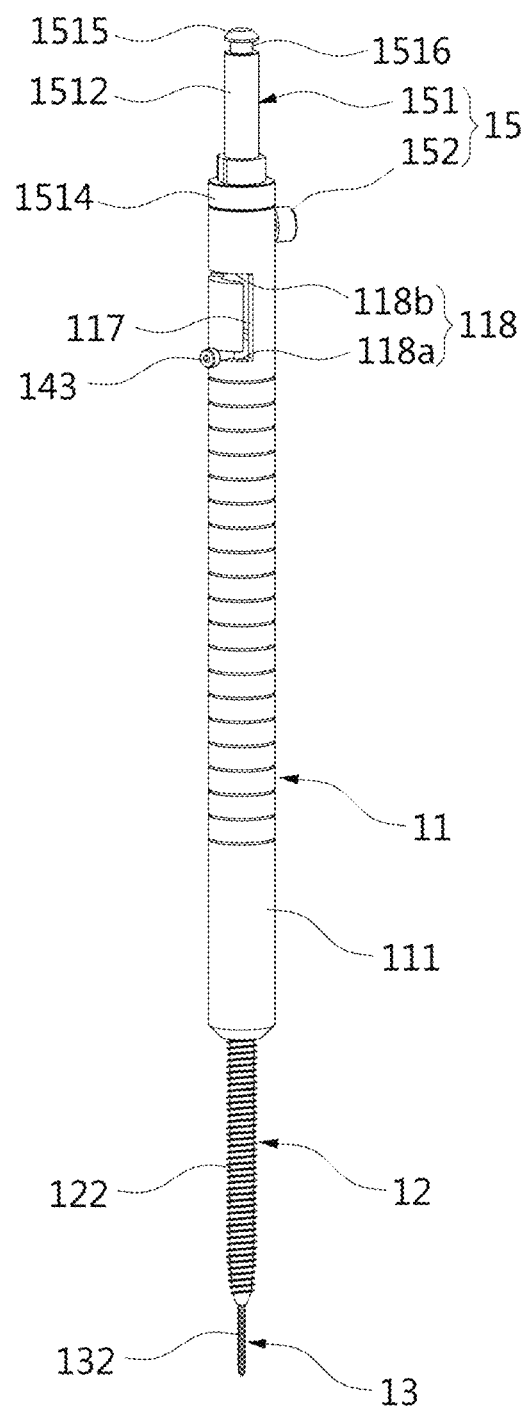
FIG. 2 is a perspective view of a medical screw surgical device according to the first embodiment of the disclosure.
Figure 3:
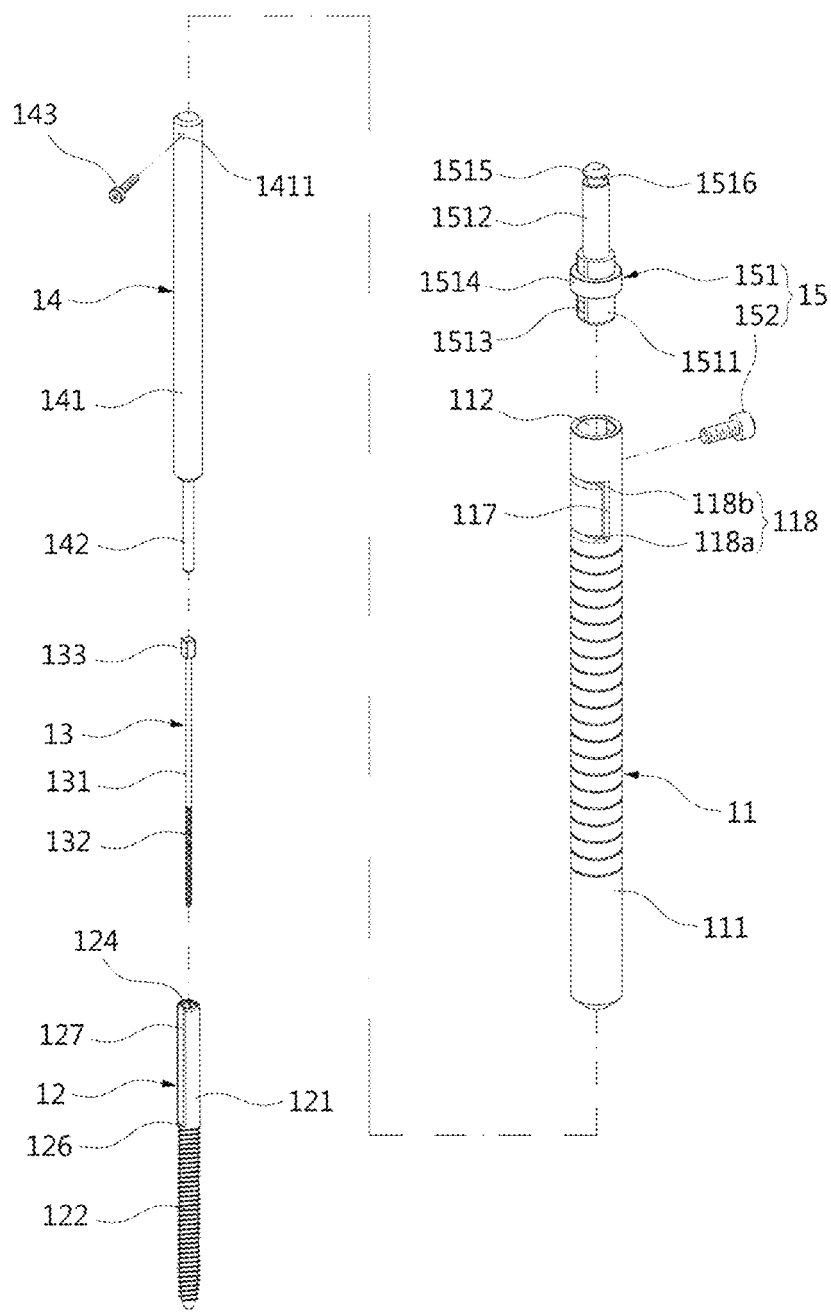
FIG. 3 is an exploded perspective view of the medical screw surgical device according to the first embodiment of the disclosure.
Figure 4A:
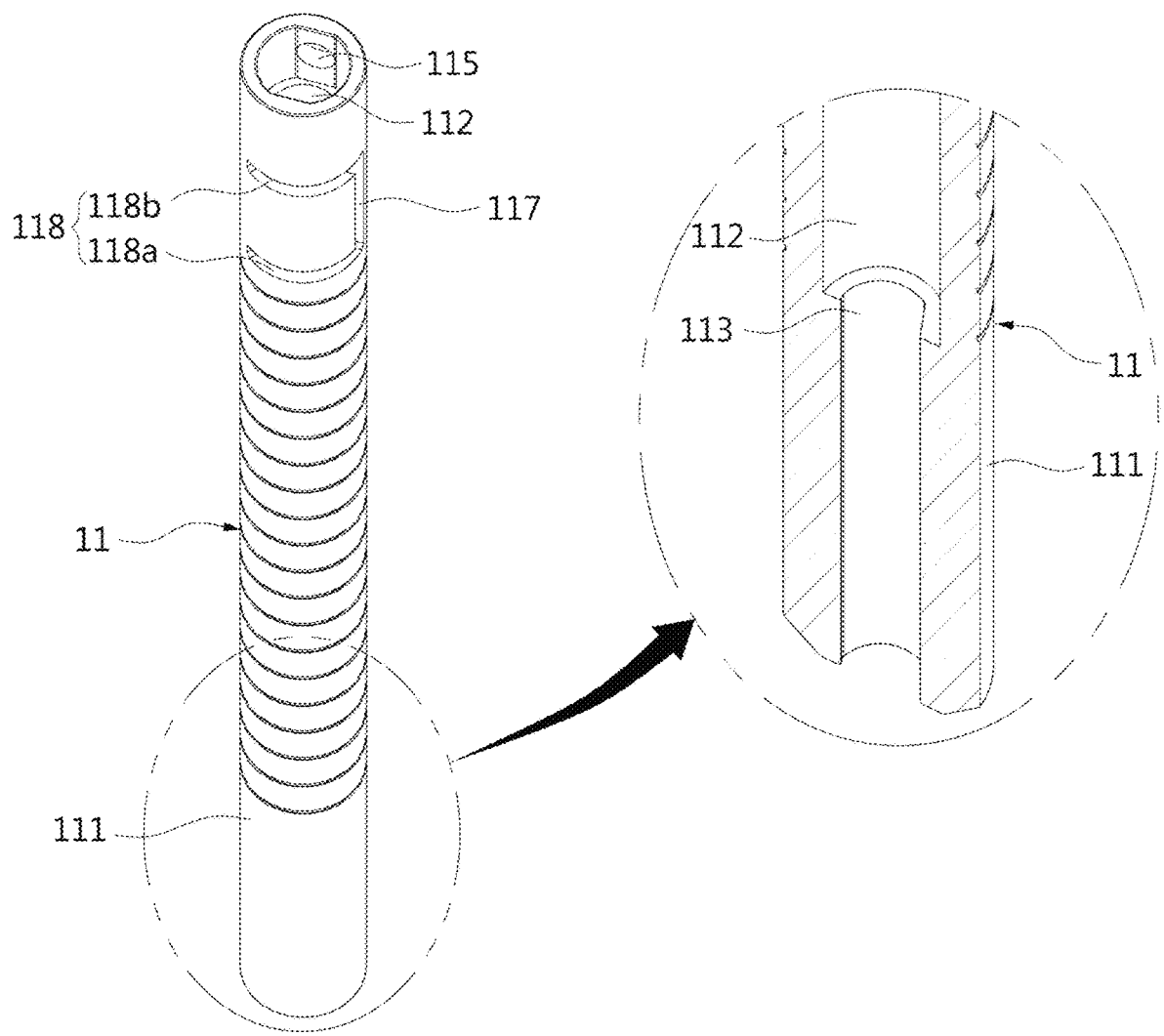
FIG. 4A is a perspective view of a surgical device main body of the medical screw surgical device according to the first embodiment of the disclosure.
Figure 4B:
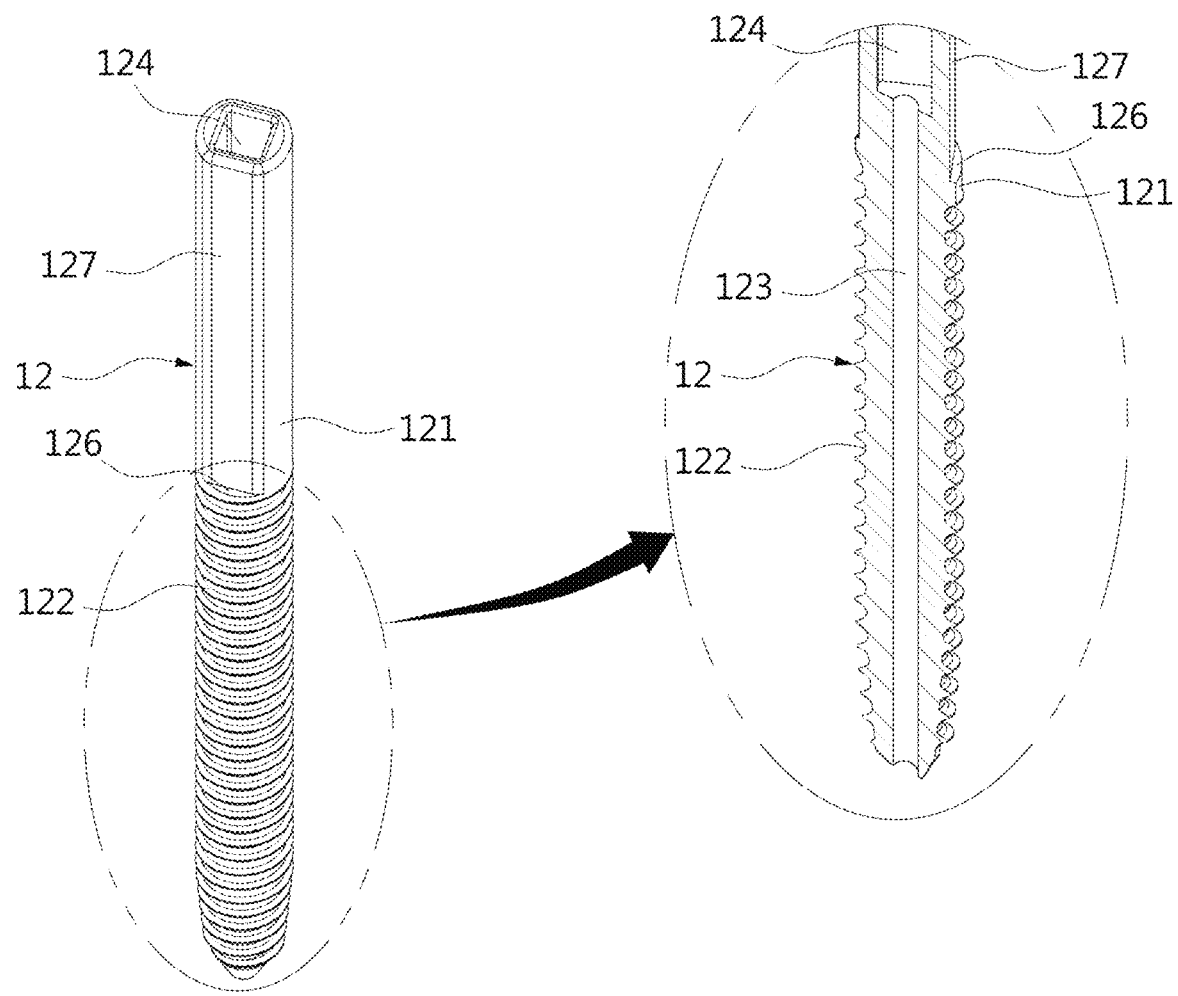
FIG. 4B is a perspective view of an extension member of the medical screw surgical device according to the first embodiment of the disclosure.
Figure 4C:
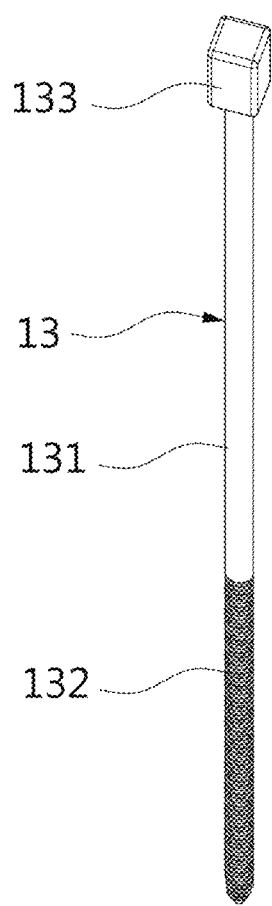
FIG. 4C is a perspective view of a guide member of the medical screw surgical device according to the first embodiment of the disclosure.

FIG. 2 is a perspective view of a medical screw surgical device according to the first embodiment of the disclosure, FIG. 3 is an exploded perspective view of the medical screw surgical device according to the first embodiment of the disclosure, FIG. 4A is a perspective view of a surgical device main body of the medical screw surgical device according to the first embodiment of the disclosure, FIG. 4B is a perspective view of an extension member of the medical screw surgical device according to the first embodiment of the disclosure, in which an enlarged view shows a partially cut-open perspective view of an indicated portion, and FIG. 4C is a perspective view of a guide member of the medical screw surgical device according to the first embodiment of the disclosure.

Referring to FIGS. 2 to 4C, a medical screw surgical device 1 according to the first embodiment of the disclosure relates to a device used in surgery for fastening a medical screw S to a human body, includes a surgical device main body 11, an extension member 12, a guide member 13 and a firing member 14, and is characterized in that not only time taken in surgery is shortened with a simple surgical process but also surgery is easily performed with simple surgical instruments.

Further, the medical screw surgical device according to the first embodiment of the disclosure is applicable to various orthopedic surgeries for a human body, but descriptions will be made based on an example of pedicle screw insertion surgery that a medial screw S typically called a pedicle screw is inserted in a pedicle P.

The surgical device main body 11 refers to an element that functions as a frame as shown in FIG. 4A, and includes an insertion passage 112 formed inside a bar-shaped body 111, and a fixing bolt fastening hole 115 formed in an upper portion thereof to which a fixing bolt 152 to be described later is fastened.

Further, the surgical device main body 11 is provided with a tool connecting member 15 on the top thereof to which an operation tool T1 (e.g. the reamer in the BACKGROUND ART) for applying a tightening force and a releasing force can be connected.

The tool connecting member 15 and the surgical device main body 11 may be formed as a single body. However, as shown in FIG. 3, the tool connecting member 15 in this embodiment includes a connection body 151 and the fixing bolt 152 so as to be detachably connected to the surgical device main body 11.

Here, the connection body 151 includes a main body connector 1511 to be inserted on the top of the surgical device main body 11, and a tool connector 1512 to connect with the operation tool T1 or the like. The main body connector 1511 includes a fixing-bolt insertion hole 1513 formed by transversely perforating a pin-shaped body thereof, and an annular stopper 1514 protruding like a ring to form a boundary with the tool connector 1512.

The tool connector 1512 may be variously shaped corresponding to a connector structure of the operation tool T1 to be connected thereto. In this embodiment, the tool connector 1512 is shaped like a round bar and formed with a stop protrusion 1515 and a holding groove 1516 at an end portion thereof to be used as being inserted in and connected to a connection hole of a control handle (see (c) in FIG. 8B, which includes a connection block T11 formed with a connection hole (not shown) and a handle T12 coupled to the connection block T11) connected to a well-known dilation tool T1 or pedicle screw driver T2 used as the operation tool in the conventional pedicle screw insertion surgery.

The fixing bolt 152 is shaped like a usual bolt that includes a fastening portion inserted in and fastened to the fixing-bolt insertion hole 1513 of the connection body 151, and a head portion through which the tightening force is applied.

Figure 1C:
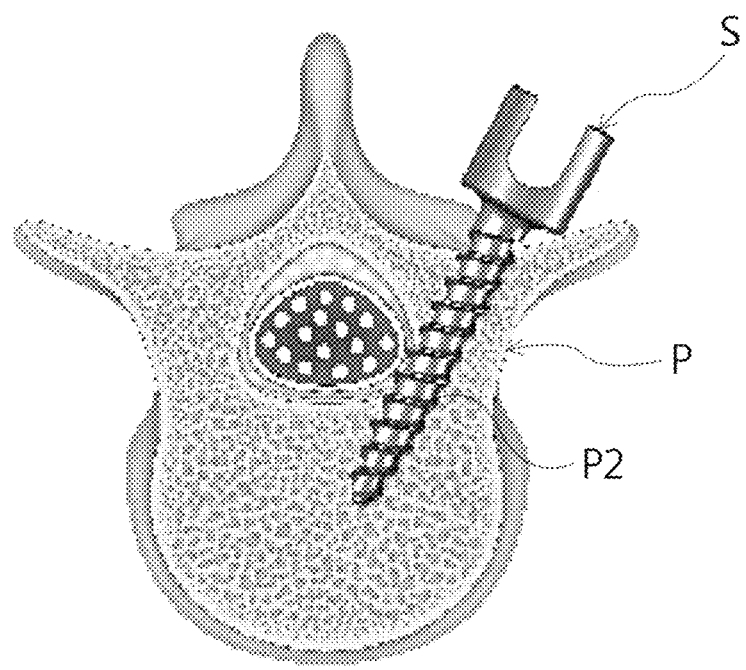
FIG. 1C is a view showing a simplified cross-section structure of a surgical site for explaining a conventional pedicle screw insertion surgery.
Figure 1D:
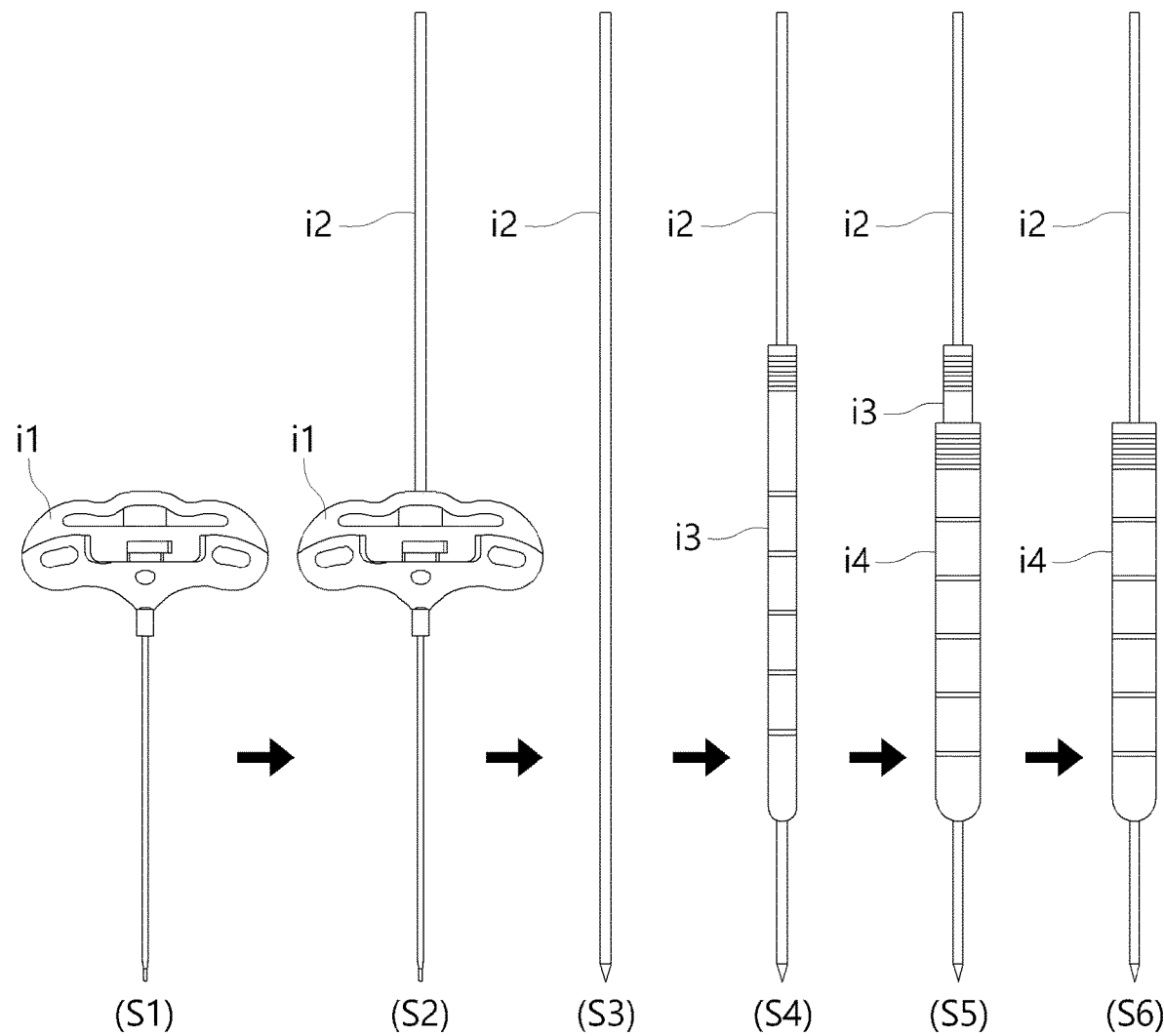
FIGS. 1D and 1E are schematic flowcharts for explaining surgical procedures of a conventional pedicle screw insertion surgery.
Figure 1E:
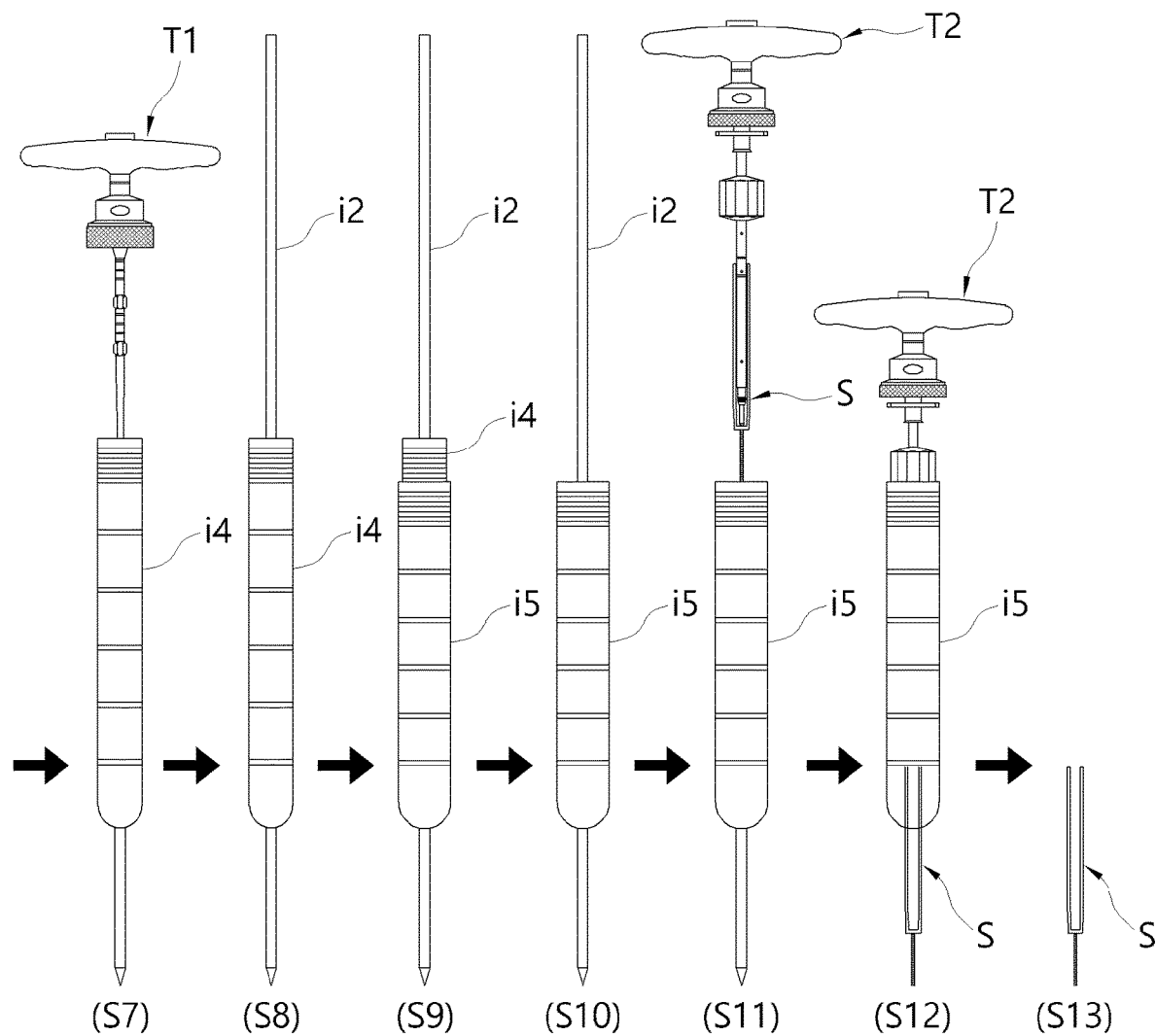

Meanwhile, the extension member 12 refers to an element that performs a reaming and tapping process to form a screw insertion hole P2, into which the medical screw S is inserted, in a surgical site such as the pedicle P as shown in FIG. 1C, and includes an extension member body 121 installed in a lower portion of the surgical device main body 11 and shaped like a round bar, and a guide hole 123 formed inside the extension member body 121.

Further, the extension member 12 includes a protrusion-movement hole 124 that communicates with the guide hole 123 and has a cross-section corresponding to the cross-section of a stopper protrusion 133 of the guide member 13 to be described later.

Here, the protrusion-movement hole 124 is formed in an upper portion of the extension member body 121 and has a range as much as protrusion (i.e. a protruding length of the guide member protruding outward from the bottom of the extension member 12) of the guide member 13, as a hole having a quadrangular cross-section with which the stopper protrusion 133 can movably mesh because the stopper protrusion 133 of the guide member 13 has a quadrangular cross-section.

In particular, the extension member 12 is formed with a screw portion for reaming and tapping in a lower portion of the extension member body 121, and this screw portion is formed as a right-handed screw on the outer circumferential surface of the extension member body 121 shaped like a pin and has a thread 122 of which a direction is opposite to a threaded direction of the guide member.

The reason why the tread 122 is formed like this as the screw portion of the extension member 12 in a direction opposite to the threaded direction of the guide member is because the extension member and the guide member need to be prevented from being inserted and moved in the same direction even through the extension member 12 is rotated interlocking with the guide member 13 as shown in FIGS. 7A to 8C, thereby preventing the guide member 13 from being further deeply inserted unintentionally. This is based on advanced technical considerations. In more detail, the screw portion of the guide member 13 to be described later has a left-handed screw portion 132. If the extension member 12 has not the right-handed screw portion but the same left-handed screw portion, the guide member 13 may also be rotated interlocking with the extension member 12 during the reaming and tapping process and thus unintentionally deeply inserted thereby causing a defective or failed surgery.

Further, the extension member 12 includes a cut-open portion 127 with a height difference 126 on the outer surface of the extension member body 121 so that a portion thereof can be inserted and locked inside the surgical device main body 11. In this case, the cut-open portion 127 is symmetrically formed at opposite sides of the extension member body 121. Like this, the cut-open portions 127 are formed at the opposite sides, and therefore the outer appearance of the extension member 12 has an approximately oval-shaped cross-section in a portion where the cut-open portion is formed.

In addition, the surgical device main body 11 includes the cut-open portion insertion hole 113 in which the cut-open portion 127 is inserted and positioned and which communicates with the insertion passage 112. The cut-open portion insertion hole 113 is formed as a hole having an approximately oval-shaped cross-section to match the shape of the cut-open portion in the lower portion of the surgical device main body 11.

Meanwhile, the guide member 13 refers to an element that is inserted in a surgical site in an initial surgical stage and performs a base hole forming function to serve as a guide pin for setting a position for forming the screw insertion hole P2 and facilitate the reaming and tapping process using the extension member. The guide member 13 is movably installed in the guide hole 123 and the protrusion-movement hole 124 of the extension member 12.

Further, the guide member 13 includes a screw portion formed in a lower portion of a guide body 131 having a pin shape and inserted in a surgical site, and the stopper protrusion 133 on a top portion of the guide body 131.

In this case, the screw portion is formed as a left-handed screw in the guide member 13, and is characterized in that its thread 132 is formed in the opposite direction to the thread of the extension member 12. The reason why the tread 132 is formed like this in the direction opposite to the threaded of the extension member 12 is because the guide member and the extension member need to be prevented from being inserted and moved in the same direction even through the guide member 13 is rotated interlocking with the extension member 12 as described in the reason of forming the right-handed screw portion 122 in the extension member 12.

The stopper protrusion 133 is formed to have a quadrangular cross-section so as to move up and down along the protrusion-movement hole 124 of the extension member 12.

Meanwhile, the firing member 14 refers to an element that is installed in the insertion passage 112 of the surgical device main body 11 and applies or releases a binding force to and from the guide member 13 to control the guide member 13 to move up and down, and includes a firing member body 141 shaped like a bar, a support bar 142 protruding from a bottom portion of the firing member body 141 to be in contact with the top portion of the guide member 13 and shaped like a bar having a smaller external diameter than the firing member body 141, and a moving piece 143 connected to the top portion of the firing member body 141.

The moving piece 143 is provided to apply an external force for moving the firing member 14 up and down. Although there are no limits to the shape of the moving piece 143 as long as the structure of the moving piece 143 is gripped and easily movable by a user, this embodiment shows that the moving piece 143 is structured as a handle screw having a head portion and a screw portion, and the firing member body 141 is formed with a fastening hole 1411 to which the handle screw is fastened in the upper end portion thereof.

Meanwhile, the surgical device main body 11 includes a movement guiding groove 117 allowing the foregoing moving piece 143 to move up and down so that the support bar 142 of the firing member 14 can press and bind the top end of the guide member 13 or release the binding force, and a holding groove 118 formed communicate with the insertion passage 112 of the surgical device main body 11.

The movement guiding groove 117 is formed as cut up and down to communicate with the insertion passage 112 of the surgical device main body 11 so that the moving piece 143 can move up and down along the movement guiding groove 117.

The holding groove 118 may be provided in plural to communicate with the movement guiding groove 117, including a first holding groove 118a perpendicularly formed in a lower end portion of the movement guiding groove 117 so that the supporter 142 of the firing member 14 can keep pressing the top portion of the guide member 13, and a second holding groove 118b perpendicularly formed in an upper end portion of the movement guiding groove 117 so that the support bar 142 of the firing member can be separated from the top portion of the guide member 13.

Figure 5:
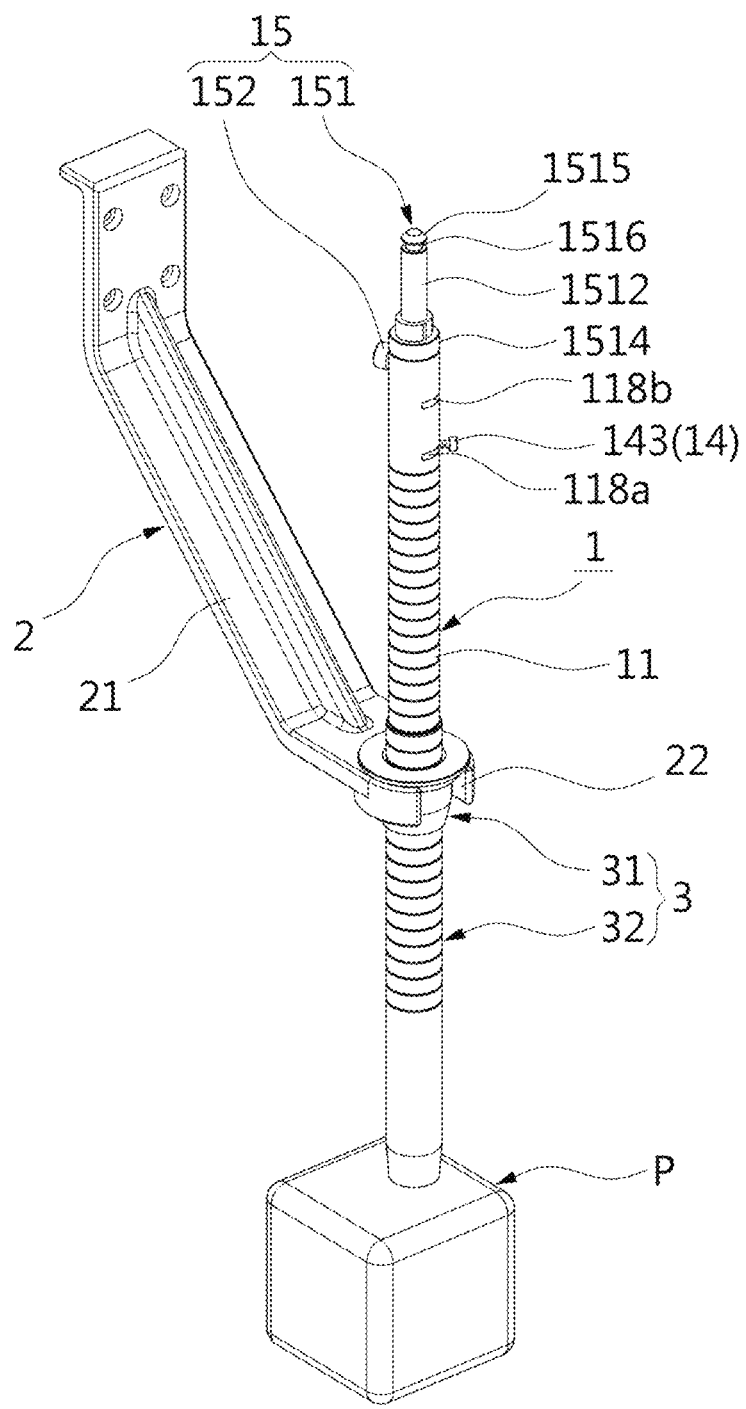
FIG. 5 is a view for describing a surgical robot with the medical screw surgical device according to the first embodiment of the disclosure.
Figure 6:
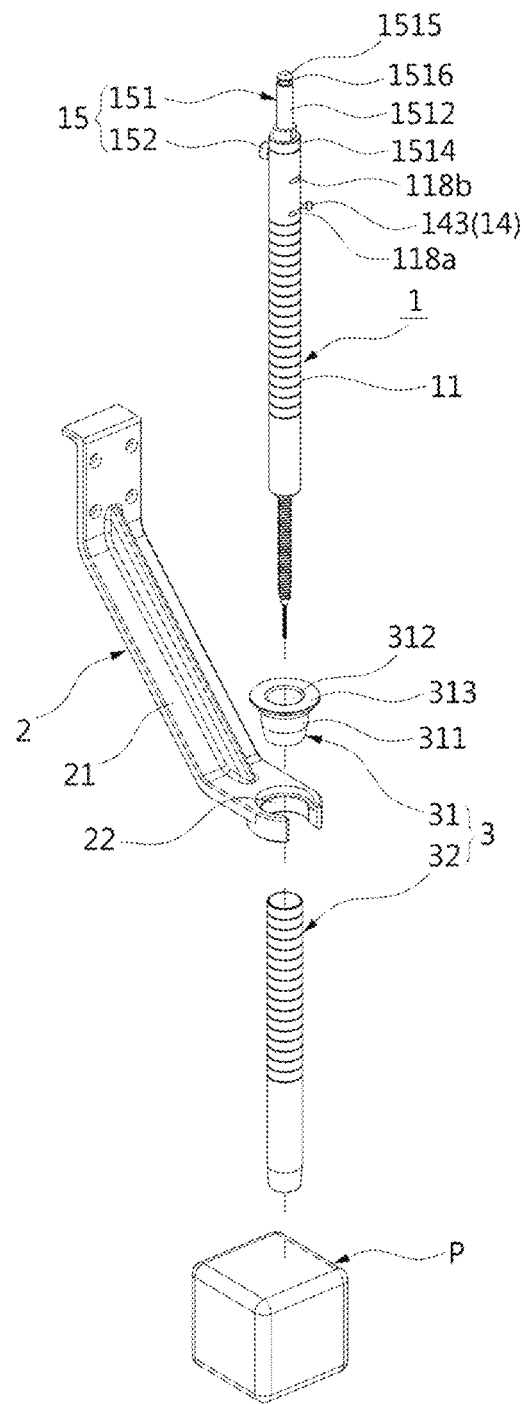
FIG. 6 is an exploded perspective view for describing the surgical robot with the medical screw surgical device according to the first embodiment of the disclosure.

FIG. 5 is a view for describing a surgical robot with the medical screw surgical device according to the first embodiment of the disclosure, as a perspective view illustrating only a part to which the medical screw surgical device is mounted, in which the pedicle P is schematically and mimetically illustrated. FIG. 6 is an exploded perspective view for describing the surgical robot with the medical screw surgical device according to the first embodiment of the disclosure Referring to FIGS. 5 and 6, the surgical robot with the medical screw surgical device according to the first embodiment of the disclosure refers to a surgical robot that is loaded with the foregoing medical screw surgical device 1 to perform surgery, and includes a support arm 2 installed in a robot arm (not shown), and a surgical device holding member 3 installed in the support arm 2 and loaded with the medical screw surgical device 1.

The support arm 2 may be variously shaped corresponding to surgical sites. In this embodiment, the support arm 2 is structured to have a coupling hole 22 at an end portion of the support arm body 21 having a curved portion corresponding to the pedicle screw insertion surgery.

The surgical device holding member 3 includes a sleeve holder 31 inserted in and locked to the coupling hole 22 of the support arm 2 and formed with a sleeve insertion hole 312, and a sleeve 32 inserted in and locked to the sleeve holder 31 and shaped like a pipe having a surgical device insertion hole.

The sleeve holder 31 includes a holder 311 shaped like a cylinder and inserted in the coupling hole 22, and a seating protrusion 313 protruding like a ring from the top end of the holder 311 and seated on a circumferential portion of the coupling hole 22 of the support arm 2.

Meanwhile, publicly-known robots for surgery, of which robot arms are moved and rotated in x, y and z directions by a driver (not shown) to perform surgery, may be selected and used for the surgical robot (not shown) without limitations. Therefore, detailed descriptions of the surgical robot will be omitted.

Figure 7A:
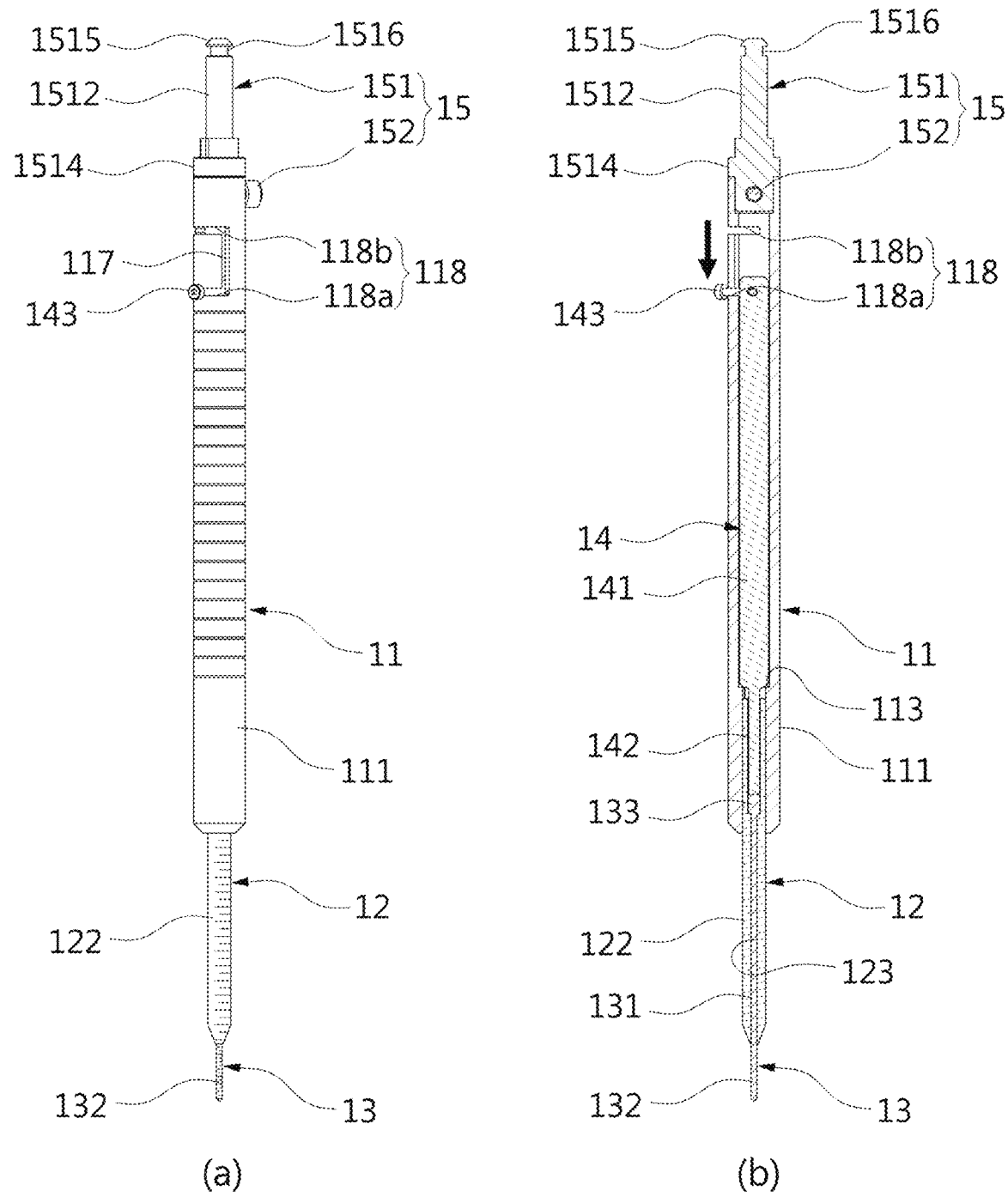
FIGS. 7A and 7B are views for describing a surgical method using the surgical robot with the medical screw surgical device according to the first embodiment of the disclosure, FIG. 7A showing a perspective view (a) and a cross-section view (b) in which the firing member of the medical screw surgical device is moved down to hold the guide member, and FIG. 7B showing cross-sectional views in which the firing member of the medical screw surgical device is moved up with (a) no loads of the guide member as the firming member is lifted (as much as height H) and (b) a lifted state of the guide member.
Figure 7B:
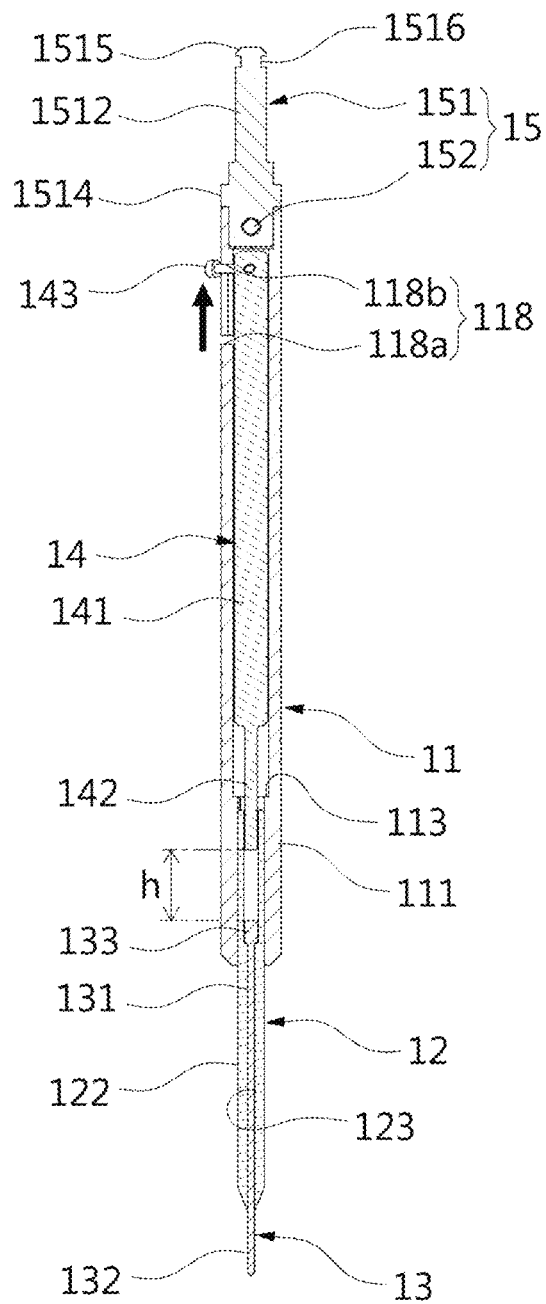
Figure 7B:
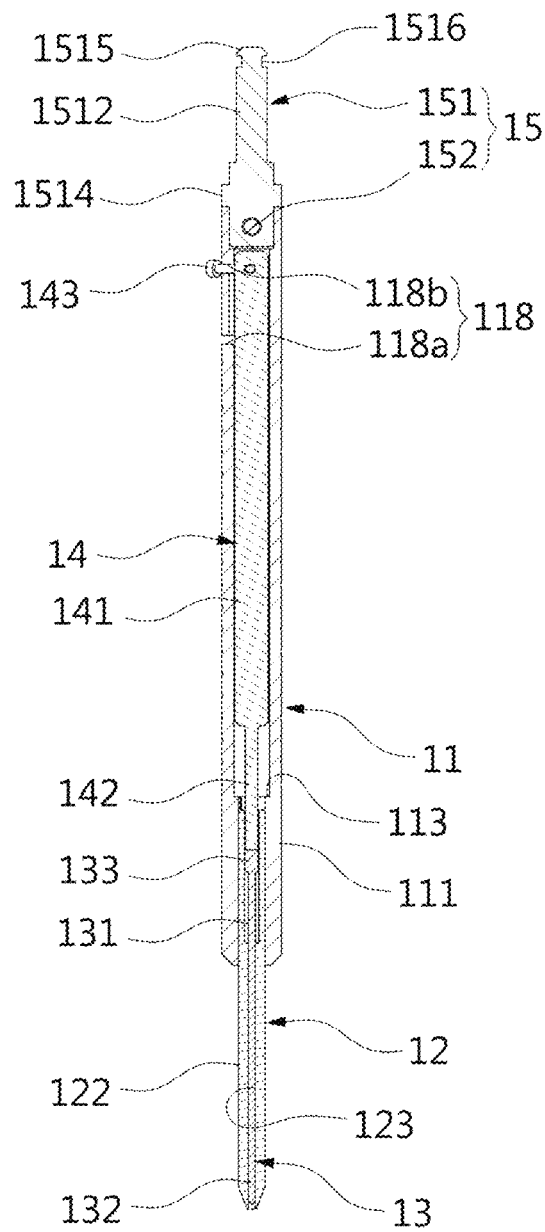

FIGS. 7A and 7B are views for describing a surgical method using the surgical robot with the medical screw surgical device according to the first embodiment of the disclosure, FIG. 7A showing a perspective view (a) and a cross-section view (b) in which the firing member of the medical screw surgical device is moved down to hold the guide member, and FIG. 7B showing cross-sectional views in which the firing member of the medical screw surgical device is moved up with (a) no loads of the guide member as the firming member is lifted (as much as height H) and (b) a lifted state of the guide member.

Figure 8A:
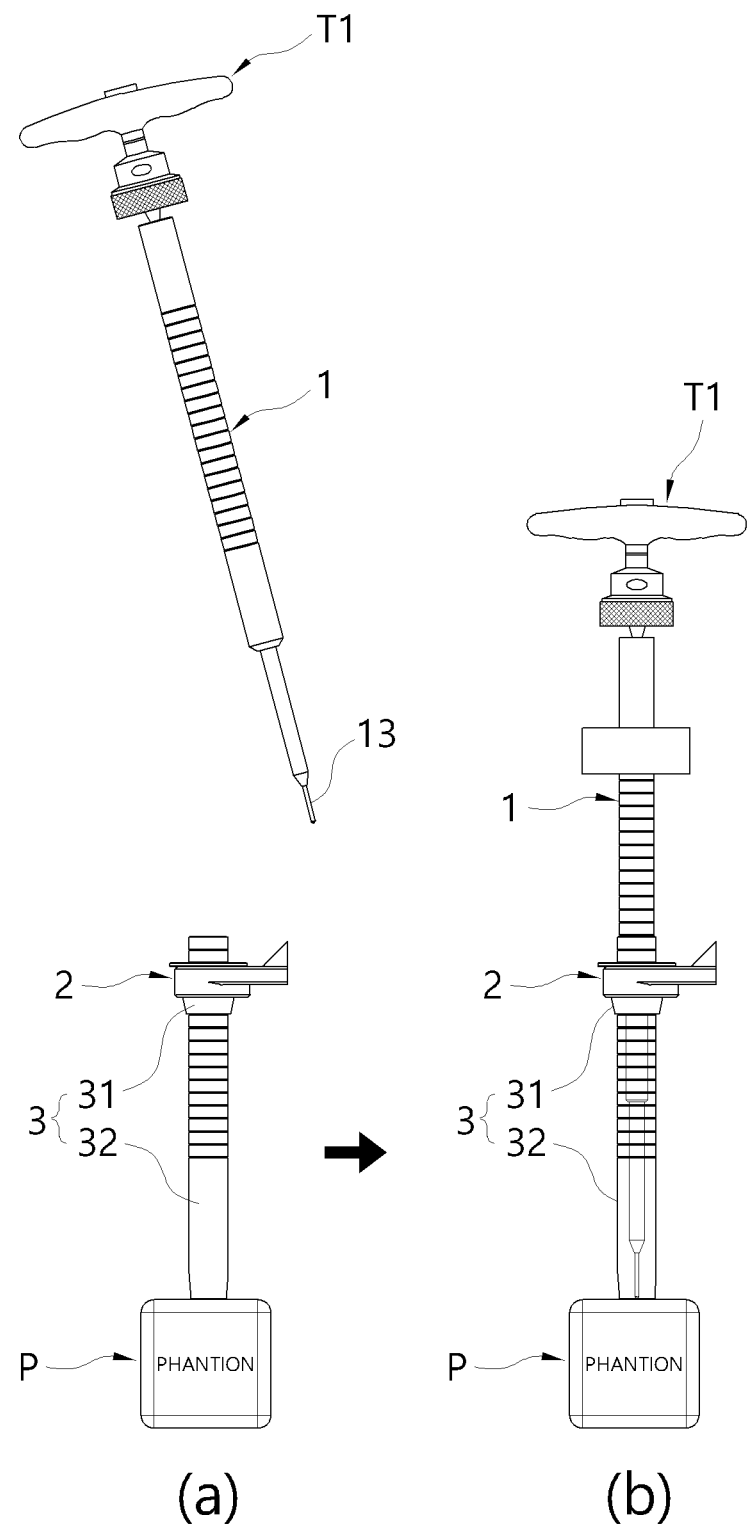
FIGS. 8A to 8C are perspective views for describing the surgical method using the surgical robot with the medical screw surgical device according to the first embodiment of the disclosure, in which the surgical processes are schematically shown in sequence.
Figure 8B:
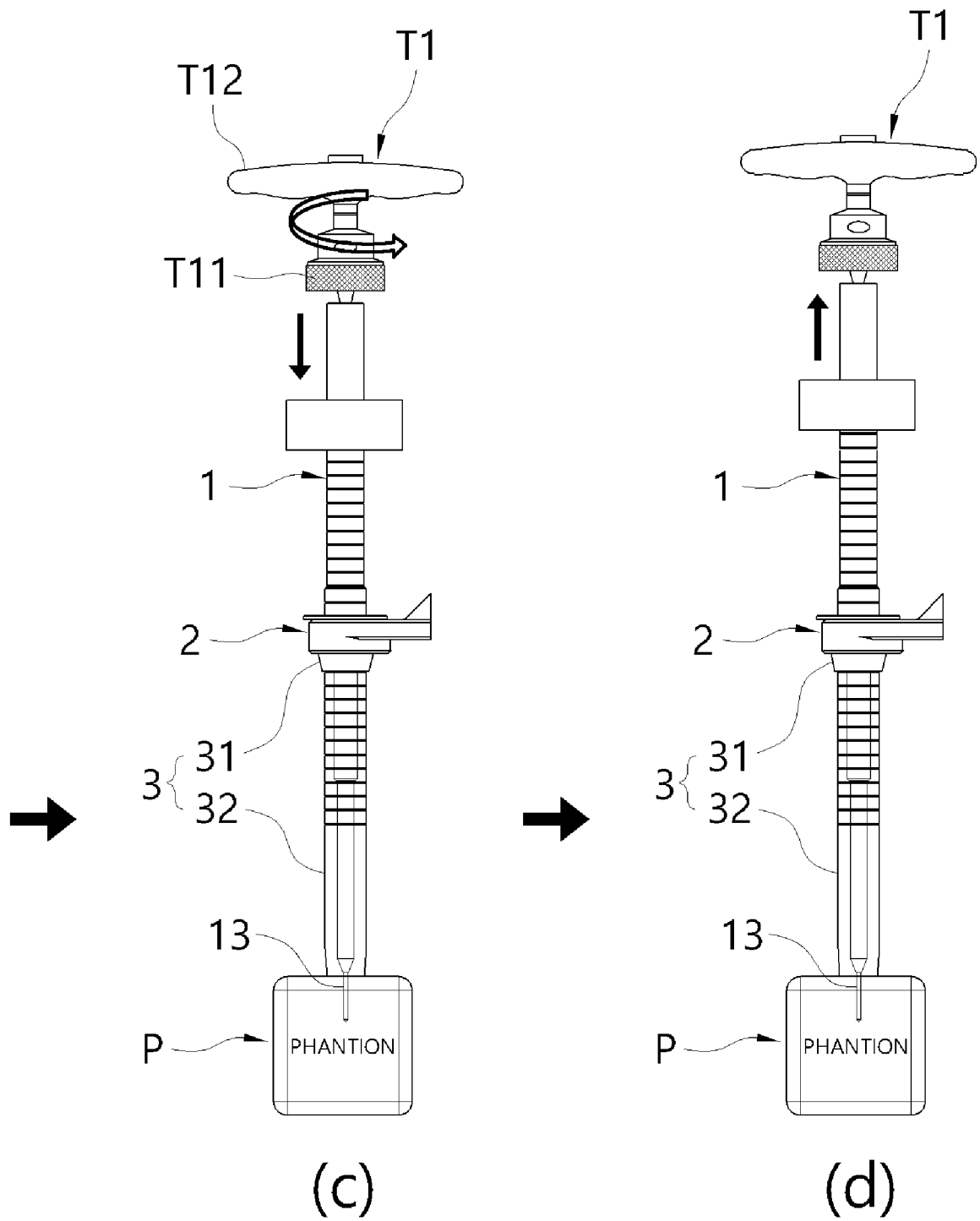
Figure 8C:
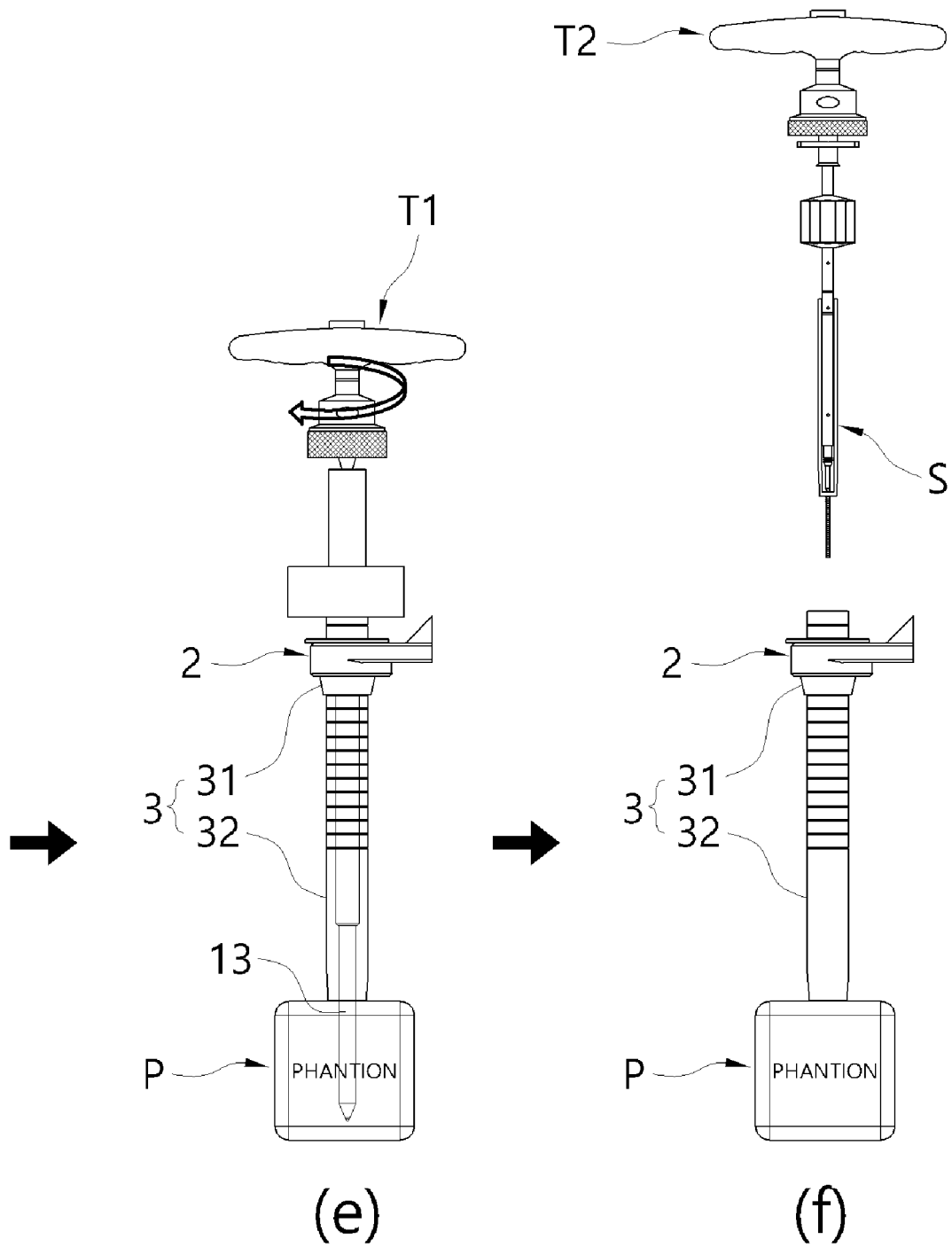

FIGS. 8A to 8C are perspective views for describing the surgical method using the surgical robot with the medical screw surgical device according to the first embodiment of the disclosure, in which the surgical processes are schematically shown in sequence.

Referring to FIGS. 7A to 8C, the surgical method of using the surgical robot with the medical screw surgical device according to the first embodiment of the disclosure performs a surgical-device mounting step, a guide-member inserting step, a guide-member releasing step, an extension-member inserting step, and a medical-screw inserting step in sequence, thereby fixing the medical screw S to a surgical site, i.e. a pedicle P.

The surgical-device mounting step refers to a step of mounting the support arm 2 to the robot arm of the surgical robot, operating the robot arm to be in position on a surgical site, using the sleeve holder 31 to couple the sleeve 32 to the support arm 2, connecting the operation tool T1 as shown in (a) of FIG. 8A to the medical screw surgical device 1 assembled as shown in FIG. 2, and inserting the medical screw surgical device 1 in the sleeve 32 as shown in (b) of FIG. 8A.

The guide-member inserting step refers to a step of moving the guide member 13 down in position by controlling the moving piece 143 of the firing member 14 in a forward direction, i.e. in a downward direction as shown in FIGS. 7A and 8B, and inserting the guide member 13 into the surgical site by applying an operational force to the operation tool.

In more detail, as shown in (b) of FIG. 7A, when the moving piece 143 moves down along the movement guiding groove 117 and enters to be held in the first holding groove 118a, the support bar 142 of the firing member 14 presses the top end of the stopper protrusion 133 of the guide member 13, thereby keeping the guide member 13 prevented from upward movement. In this case, when the operation tool T1 is rotated counterclockwise, the left-handed screw portion 132 of the guide member 13 burrows into and is inserted in the pedicle at a preset depth.

The guide-member releasing step refers to a step of controlling the firing member 14 in a reverse direction, i.e. an upward direction, and releasing the binding force applied to the guide member 13 so that the guide member 13 can move upward. In other words, as shown in (a) of FIG. 7B, when the moving piece 143 moves up along the movement guiding groove 117 and enters to be held in the second holding groove 118b, the support bar 142 of the firing member 14 is separated from the top end of the stopper protrusion 133 of the guide member 13, thereby releasing the binding force and allowing the guide member 13 to move upward with no loads.

The extension-member inserting step refers to a step of applying the tightening force to the operation tool T1 so that the extension member 12 can ream and tap the surgical site and form the screw insertion hole P2, in which, when the operation tool T1 is rotated clockwise as shown in (e) of FIG. 8C, the right-handed screw portion 122 of the extension member 12 burrows into and is inserted in the pedicle at a preset depth, thereby reaming and tapping the screw insertion hole. In this case, the guide member 13 not only has no-load condition based on the guide-member releasing step but also is formed with the left-handed screw portion 132, and is therefore not unintentionally inserted in the pedicle any more even while the operation tool T1 is rotated clockwise, thereby entering a state as shown in (b) of FIG. 7B.

The medical-screw inserting step refers to a step of removing the operation tool T1 including the foregoing medical screw surgical device 1, inserting and fastening the screw coupling tool T2 (typically called the screw driver) with the medical screw S through the sleeve 332 of the surgical device holding member 3, and removing the screw coupling tool T2 when the medical screw S is completely inserted.

As described above, when the pedicle screw insertion is performed in the pedicle screw insertion surgery by the surgical method of using the surgical robot with the medical screw surgical device according to the first embodiment of the disclosure, the surgery is performed by the concise and simple steps including the surgical-device mounting step, the guide-member inserting step, the guide-member releasing step, the extension-member inserting step and the medical-screw inserting step.

Accordingly, surgical procedures and time taken in surgery are remarkably reduced, and only the surgical instruments such as the medical screw surgical device 1, the general operation tool T1 used as the reamer, and the screw coupling tool T2 called the screw driver are needed without many kinds of surgical instruments such as the guide pin, the reference wire, the first sleeve, the second sleeve, the third sleeve, the reamer, the hammer, etc. conventionally required in the surgery, thereby reducing management and maintenance costs and thus decreasing a burden of medical expenses on a patient.

Further, during the pedicle screw insertion surgery, the medical screw surgical device 1 is coupled to the support arm 2 mounted to the robot arm of the surgical robot, and the operation tool is coupled and rotated as described above to form the screw insertion hole, thereby having advantages of omitting manual operations such as striking the guide pin with a hammer. The guide member 13 is inserted only at a preset depth, thereby solving a conventional problem caused when it is unintentionally further deeply inserted. The medical screw is inserted through guide operations of the surgical robot, thereby preventing a defective surgery and securing accuracy. Radiography is minimized, thereby having advantages of reducing exposure to radiation.

The foregoing descriptions are merely one embodiment of carrying out a medical screw surgical device, a surgical robot with the same, and a surgical method of using the surgical robot with the medical screw surgical device, and the disclosure is not limited to the foregoing embodiment, but the technical concept of the disclosure covers up to a range in which various changes can be made by anyone having ordinary knowledge in the art to which the disclosure pertains without departing from the gist of the disclosure defined in the following claims.

The terms used in the foregoing embodiment are only used to describe a specific embodiment, and not intended to limit the disclosure. Singular forms are intended to include plural forms unless otherwise mentioned contextually. In the disclosure, it will be understood that the terms "include", "have", etc. are to include the presence of features, numbers, steps, operations, elements, components or combination thereof, but do not preclude the presence or addition of one or more other features, numbers, steps, operations, elements, components or combination thereof.

The invention claimed is:

1. A medical screw surgical device comprising:
   a surgical device main body having a shape of an elongated round bar and having an insertion passage formed therein;
   a bone screw extending from a lower portion of the surgical device main body and having a guide hole formed therein;
   a guide shaft movably disposed in the guide hole of the bone screw; and
   a guide controller disposed in the insertion passage of the surgical device main body,
   wherein the guide controller includes a guide controller body in a shape of an elongated round bar and a moving piece protruding from a top portion of the guide controller body to enable the guide controller to control the guide shaft to move up and down by moving the moving piece up and down.

2. The medical screw surgical device according to claim 1, further comprising a tool connecting member disposed in an upper portion of the surgical device main body and configured to connect with an operation tool for applying a tightening force and a releasing force to the surgical device main body.

3. The medical screw surgical device according to claim 2, wherein
   the tool connecting member comprises a connection body and a fixing bolt, the connection body comprising a main body connector which is inserted in a top portion of the surgical device main body and having a fixing-bolt insertion hole formed therein, and a tool connector to which the operation tool is connected, and the fixing bolt being inserted in the fixing-bolt insertion hole of the connection body, and
   the surgical device main body comprises a fixing bolt fastening hole in an upper portion thereof to which the fixing bolt is fastened.

4. A surgical robot, comprising:
   a robot arm;
   a support arm provided in the robot arm;
   a surgical device holding member provided in the support arm; and
   the medical screw surgical device according to claim 3, provided in the surgical device holding member.

5. The surgical robot according to claim 4, wherein
   the support arm comprises a coupling hole at an end portion of a support arm body comprising a curved portion, and
   the surgical device holding member comprises a sleeve holder configured to be inserted in and locked to the coupling hole and having a sleeve insertion hole, and a sleeve configured to be inserted in the sleeve holder and comprising a surgical device insertion hole.

6. A surgical robot, comprising:
   a robot arm;
   a support arm provided in the robot arm;
   a surgical device holding member provided in the support arm; and
   the medical screw surgical device according to claim 2, provided in the surgical device holding member.

7. The surgical robot according to claim 6, wherein
   the support arm comprises a coupling hole at an end portion of a support arm body comprising a curved portion, and
   the surgical device holding member comprises a sleeve holder configured to be inserted in and locked to the coupling hole and having a sleeve insertion hole, and a sleeve configured to be inserted in the sleeve holder and comprising a surgical device insertion hole.

8. The medical screw surgical device according to claim 1, wherein
   the guide shaft comprises a guide body having a pin shape and a screw portion formed on an outer circumferential surface of the guide body, and
   the bone screw comprises a bone screw body having a pin shape and a screw portion formed on an outer circumferential surface of the bone screw and threaded in an opposite direction to the screw portion of the guide shaft.

9. The medical screw surgical device according to claim 8, wherein
   the guide shaft comprises a stopper protrusion formed in a top portion of the guide body, and
   the bone screw comprises a protrusion-movement hole formed to have a cross-section corresponding to a cross-section of the stopper protrusion and communicating with the guide hole.

10. A surgical robot, comprising:
    a robot arm;
    a support arm provided in the robot arm;
    a surgical device holding member provided in the support arm; and
    the medical screw surgical device according to claim 9, provided in the surgical device holding member.

11. The surgical robot according to claim 10, wherein
the support arm comprises a coupling hole at an end portion of a support arm body comprising a curved portion, and
the surgical device holding member comprises a sleeve holder configured to be inserted in and locked to the coupling hole and having a sleeve insertion hole, and a sleeve configured to be inserted in the sleeve holder and comprising a surgical device insertion hole.

12. The medical screw surgical device according to claim 8, wherein
the bone screw comprises a flat portion on an outer circumferential surface of the bone screw body, and
the insertion passage of the surgical device main body is formed with a flat portion insertion hole in which the flat portion is inserted and seated.

13. A surgical robot, comprising:
a robot arm;
a support arm provided in the robot arm;
a surgical device holding member provided in the support arm; and
the medical screw surgical device according to claim 12, provided in the surgical device holding member.

14. A surgical robot, comprising:
a robot arm;
a support arm provided in the robot arm;
a surgical device holding member provided in the support arm; and
the medical screw surgical device according to claim 8, provided in the surgical device holding member.

15. The surgical robot according to claim 14, wherein
the support arm comprises a coupling hole at an end portion of a support arm body comprising a curved portion, and
the surgical device holding member comprises a sleeve holder configured to be inserted in and locked to the coupling hole and having a sleeve insertion hole, and a sleeve configured to be inserted in the sleeve holder and comprising a surgical device insertion hole.

16. The medical screw surgical device according to claim 1, wherein
the guide controller further comprises a support bar protruding from a bottom portion of the guide controller body and being in contact with a top portion of the guide shaft, and
a movement guiding groove, which allows the moving piece to move up and down, and holding grooves, which communicate with the movement guiding groove and hold the moving piece in position, are formed to communicate with the insertion passage of the surgical device main body.

17. A surgical robot, comprising:
a robot arm;
a support arm provided in the robot arm;
a surgical device holding member provided in the support arm; and
the medical screw surgical device according to claim 1, provided in the surgical device holding member.

18. The surgical robot according to claim 17, wherein
the support arm comprises a coupling hole at an end portion of a support arm body comprising a curved portion, and
the surgical device holding member comprises a sleeve holder configured to be inserted in and locked to the coupling hole and having a sleeve insertion hole, and a sleeve configured to be inserted in the sleeve holder and comprising a surgical device insertion hole.

* * * * *